United States Patent [19]

Vazopolos

[11] 3,959,360
[45] May 25, 1976

[54] PROCESS FOR PREPARING 1-HYDROXY, ETHYLIDENE-1,1-DIPHOSPHONIC ACID

[75] Inventor: Steve Vazopolos, St. Louis, Mo.

[73] Assignee: Monsanto Company, St. Louis, Mo.

[22] Filed: July 31, 1975

[21] Appl. No.: 600,691

[52] U.S. Cl. .................. 260/502.4 A; 260/541; 260/544 Y; 423/488
[51] Int. Cl.$^2$ .......................... C07F 9/38
[58] Field of Search ..................... 260/502.4 A

[56] References Cited
UNITED STATES PATENTS

| | | | |
|---|---|---|---|
| 3,202,579 | 8/1965 | Berth et al. | 260/502.4 A |
| 3,270,064 | 8/1966 | Inaba et al. | 260/631 R |
| 3,366,677 | 1/1968 | Quimby | 260/502.4 A |
| 3,409,510 | 11/1968 | Master et al. | 260/643 R |
| 3,449,409 | 6/1969 | Irani et al. | 260/502.4 A |

FOREIGN PATENTS OR APPLICATIONS

| | | | |
|---|---|---|---|
| 978,297 | 12/1964 | United Kingdom | 260/502.4 A |
| 276,947 | 10/1970 | U.S.S.R. | 260/502.4 A |

*Primary Examiner*—Joseph E. Evans
*Attorney, Agent, or Firm*—Thomas B. Leslie

[57] ABSTRACT

A process for preparing 1-hydroxy, ethylidene-1,1-diphosphonic acid, which comprises contacting a phosphorus trihalide such as phosphorus trichloride with glacial acetic acid in a reaction zone maintained at a temperature of from about 50°C. to about 80°C. while continuously removing by-product acetyl halide as formed from the said reaction zone to form a single-phase liquid reaction product, heating said reaction product to a temperature of from 90°C. to 140°C. and reacting therewith acetic anhydride to form a normally solid anhydrous reaction product, and hydrolyzing said product by steam treatment to recover the desired 1-hydroxy, ethylidene-1,1-diphosphonic acid and remove by-product acetic acid. The acetyl halide by-product is recovered by absorbing same in the aqueous by-product acetic acid recovered from the hydrolysis step and thereby recovering glacial acetic acid for storage and recycle to the process. The process is adapted for continuous operation.

21 Claims, No Drawings

PROCESS FOR PREPARING 1-HYDROXY, ETHYLIDENE-1,1-DIPHOSPHONIC ACID

BACKGROUND OF THE INVENTION

This invention relates to processes for preparing phosphonic acids and, more particularly, to an improved process for preparing 1-hydroxy, ethylidene-1,1-diphosphonic acid.

Various processes have been suggested in the past for the production of such 1-hydroxy, organo-1,1-diphosphonic acids as 1-hydroxy, ethylidene-1,1-diphosphonic acid but all of these prior suggested processes suffer from one or more disadvantages, either technical or economic. Most of the prior art processes for the production of these diphosphonic acids are carried out batch-wise and do not lend themselves to continuous operation. They likewise suffer from the disadvantage of gross underutilization of reaction equipment in most instances and relatively long and inefficient process cycle times. Such processes have involved handling and storage of large amounts of carboxylic acid halides which in such concentrations pose safety hazards in the handling thereof.

Even those prior art processes which are adaptable to continuous operation suffer certain disadvantages which render them unattractive for commercial installation. For example, the process disclosed in U.S. Pat. No. 3,366,677 of Quimby utilizes the expensive reagents phosphorous acid and acetic anhydride as well as acetyl chloride and requires the use of from 3 to 8 times the molar ratio of acetic anhydride to phosphorous acid making the process particularly expensive to carry out. Further prior art continuous processes such as that disclosed in U.S. Pat. No. 3,449,409 of Irani and Mitchell require operation at a temperature sufficiently low as to contain a two-phase reaction mixture containing a separate liquid phase of carboxylic acid halide and, subsequently thereto, the removal, storage and recharging of such acid halide to the reaction mixture in a subsequent reaction vessel. These procedures lead to disadvantages. The handling, storage and recharging of the acid halide constitutes a safety hazard as mentioned hereinabove. Thus, improved processes which can be carried out continuously with improved equipment utilization, improved safety and shorter reaction cycle times have been desired.

SUMMARY OF THE INVENTION

It is a principal object of the present invention to provide a novel process for preparing 1-hydroxy, ethylidene-1,1-diphosphonic acid in an improved manner.

Another object of this invention is to provide a process for preparing 1-hydroxy, ethylidene-1,1-diphosphonic acid which is adaptable for continuous operation.

A further object of this invention is to provide a process for preparing 1-hydroxy, ethylidene-1,1-diphosphonic acid which, among other things, results in improved utilization of equipment, improved safety and a more efficient process in terms of overall cycle times.

These and other objects will become apparent from the following detailed description.

It has now been found that 1-hydroxy, ethylidene-1,1-diphosphonic acid can be prepared advantageously by reacting a lower aliphatic monocarboxylic acid and a phosphorus trihalide under such conditions that the reaction mixture and the by-product acetyl halide thus produced is continuously removed as it is produced from said reaction mixture as will be more fully discussed hereinafter. By following the teachings of the present invention, many advantages including the above objects are realized.

DESCRIPTION OF PREFERRED EMBODIMENTS

The following equation represents the overall reaction utilizing phosphorus trichloride as the phosphorus trihalide reactant and stoichiometric amounts of the reactants:

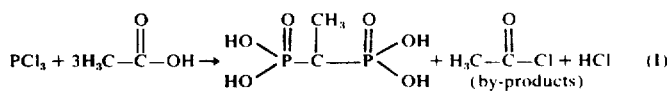

The compound prepared by the process of the present invention and illustrated above is termed 1-hydroxy, ethylidene-1,1-diphosphonic acid and can also be termed ethane, 1-hydroxy, 1,1-diphosphonic acid. Such compound has been found to be useful as a sequestering agent for heavy metal cations, scale inhibiting agent and corrosion inhibiting agent in aqueous systems.

In general, the process of the present invention is directed to reacting in a reaction zone glacial acetic acid and a phosphorus trihalide at a temperature above the boiling point in the reaction mixture of the by-product acetyl halide produced and continuously removing the by-product acetyl halide as formed from said reaction zone to form a homogeneous, single-phase liquid reaction product, heating this liquid reaction product in a reaction zone to an elevated temperature above about 90°C., adding and reacting with said liquid reaction product acetic anhydride whereby a normally solid anhydrous reaction product is formed, and thereafter recovering the desired product, 1-hydroxy, ethylidene-1,1-diphosphonic acid, from the normally solid anhydrous reaction product by steam treatment.

The liquid reaction product which is first formed in the process of the present invention by reacting the acetic acid and phosphorus trihalide is believed to be essentially or predominantly phosphorous acid (including ortho and pyrophosphorous acid and mixtures of these) and acetylated derivatives thereof, usually in minor amounts, and containing, in addition, by-product acetyl halide, hydrogen halide acids (HBr or HCl), unreacted acetic acid and the like. This reaction product can be prepared by mixing or blending the acetic acid and phosphorus trihalide in a molar ratio of at least about 2.5:1, preferably at least 3.0:1 and most preferably from about 3.1 to 3.5:1, i.e., excess amounts of acetic acid such as about 10% to about 40% by weight of the reactants are often desirable.

The reaction is carried out under temperatures which are sufficient to maintain the mixture of reactants and reaction product liquid and which are above the boiling point of the by-product acetyl halide in order to substantially remove it as produced, i.e., up to the boiling point of the reaction mixture but below the boiling point of the PX$_3$ reactant. Such temperatures are usually from about 50°C. to about 80°C. with the temperatures of from about 50°C. to about 70°C. being especially preferred.

In preparing the desired phosphonic acid by using other methods, the reactions are often exothermic and thus difficult to control and handle; however, the preferred reaction is endothermic and thus such advantages as better control of process conditions, faster reaction times and the like result from the process of the present invention.

It has been found desirable when operating the initial reaction above the boiling point of the acetyl halide by-product to employ an antifoam agent to suppress foaming which may occur depending on the rate of addition of the phosphorus trihalide and acetic acid reactants. Such foaming due to rapid evolution of acetyl halide and hydrogen halide in vapor form can lead to entrainment therewith of freshly charged reactants, particularly phosphorus trihalide, with consequent variation in the desired mole ratios of reactants. For the purposes of suppressing such foaming and avoiding any entrainment addition of an antifoam agent is desirable. The antifoam agent can be any such agent inert to the reaction, and is preferably a silicone antifoam. Typical examples of suitable antifoams are the polysiloxanes and polydimethylsiloxanes such as SAG-470 of Union Carbide Corporation, SWS-214 of Stauffer Chemical Company and Antifoam H-10 Emulsion of Dow-Corning Corporation. The antifoam agent can conveniently be charged to the reaction zone intermittently or continuously generally in amounts of from about 10 to about 200 ppm based on the weight of the desired final product diphosphonic acid, and preferably from about 10 to 50 ppm on active siloxane based on such final product produced.

The liquid reaction product as hereinbefore described is then heated to elevated temperatures which are generally in the range of about 90°C. to about 180°C. depending upon the particular reactants used, and preferably from about 90°C. to about 140°C., and under atmospheric pressure, although sub-atmospheric pressure as well as pressures in excess of atmospheric can be used. During this temperature increase, further remaining by-product acetyl halide and hydrogen halide remaining in the liquid reaction product is evolved from the liquid reaction product.

While the reactant product is being maintained under the foregoing temperatures and conditions, i.e., heated to at least about 90°C., there is added and reacted with the liquid reaction product acetic anhydride. The acetic anhydride can be added as a liquid in any manner to the liquid reaction product, but it is preferably added below the exposed surface of the liquid product, i.e., for example, below the surface from which vapors are evolved during heating. Although there may be some advantages seen by adding the acid anhydride to the vapor being evolved from the liquid portion of the product during heating, this procedure is not preferred. Although it has been disclosed that acetyl halide could be reacted at this step in place of acetic anhydride, such is not preferred in the present process due to the extra process steps required. A sufficient quantity of acetic anhydride is added to the liquid reaction product to produce the desired normally solid anhydrous reaction product. It is undesirable, however, to add a sufficient quantity of acetic anhydride which, at the temperature of the reaction zone, causes the reaction mixture to become too viscous to stir, which condition can occur. When such condition does occur it is necessary generally to stop the reaction process and begin the recovery procedure by addition of water in order to lower the viscosity. The quantities generally required for carrying out the process at the above temperature conditions range from about 0.3 to about 0.6 moles of acetic anhydride per mole of phosphorus trihalide charged in the initial reaction. More preferably, the acetic anhydride is charged in a molar ratio of from about 0.4 to about 0.5 moles per mole of phosphorus trihalide reactant.

A normally solid, i.e., a solid mass at room temperature of about 25°C., anhydrous reaction product is formed by the foregoing described heating and acetic anhydride reaction steps which usually contains, in addition to some of the desired product or derivatives thereof, a complex mixture of products believed to be condensed or dehydrated species, such as polymers, of the desired product, and in some cases excess or unreacted residual phosphorous acid.

The desired 1-hydroxy, ethylidene-1,1-diphosphonic acid can be recovered from the normally solid anhydrous reaction product by various known methods. For the purpose of the present invention, however, the desired product is recovered by steaming, with or without the use of water in addition. The anhydrous reaction product can be treated with steam while being maintained at elevated temperatures, i.e., above about 100°C. and preferably from about 115°C. to about 150°C., and under atmospheric pressure, although sub-atmospheric pressures as well as pressures in excess of atmospheric can be used, thereby volatilizing off the acetic acid present which is collected for reuse for the recovery of the acetyl halide by-product as more fully described below, as well as hydrating any of the condensed or dehydrated species of the desired product which are present. This steaming step yields an aqueous, usually highly concentrated, solution or slurry of the desired product, preferably greater than about 50% by weight. The steam treatment can be carried out by steaming, that is, by passing or introducing steam at a temperature of from about 100°C. to about 200°C., and preferably in the range of from about 110°C. to about 150°C., into the anhydrous product in such a manner as to establish intimate contact of the anhydrous product with the steam such as by steam sparging and the like.

Depending upon the reaction conditions and the amount of acetic anhydride added to the liquid reaction product, in some cases, particularly when operating in a batch-wise manner, it may be desirable to add water to the normally solid anhydrous reaction product prior to recovering the desired product therefrom. The amount of water which can be added can vary but is usually in an amount which will cause the exothermic reaction of the anhydrous product due to the addition of the water to substantially subside or cease. Such amount is usually from about 5% to about 40% by weight of the anhydrous product and preferably from about 10% to about 20% by weight thereof. It has been found generally desirable when operating in the batch-wise manner to add this amount of water to the normally solid anhydrous reaction product prior to recovery thereof by steaming.

As indicated above, the desired product, 1-hydroxy, ethylidene-1,1-diphosphonic acid, is produced by the steam treatment step in the form of a highly concentrated aqueous solution with very slight amounts of residual acetic acid and phosphorous acid present within the aqueous medium. The 1-hydroxy, ethylidene-1,1-diphosphonic acid, normally solid at room temperature, may be recovered from the aqueous medium, if desired, as crystals, by various methods such as removing the water by evaporation including vacuum evaporation, allowing the product to crystallize by cooling a relatively hot saturated aqueous solution, allowing the product to crystallize from a saturated solution by seeding the solution, or precipitating by the addition of a miscible solvent in which the product is less soluble, such as methanol, ethanol, acetone and the like. The amorphous form of the product can be formed when the water of solution is quickly removed under high temperature conditions such as by flash drying, drum drying and the like.

In the process of the present invention it is generally desirable to recover the acetyl halide by-product derived from the initial reaction step and the acetic acid by-product hydrolyzed and vaporized from the recovery step for economic reasons. The acid values of both these by-products are made available by recovery for reuse in the process. The recovery of these valuable by-products is achieved by contacting the acetyl halide with the aqueous solution of acetic acid from the product recovery step wherein the normally solid anhydrous reaction product is subjected to the steam treatment. The amounts of water charged initially in this product recovery step, if employed, and the amount of steam employed in that recovery is conveniently controlled to produce an aqueous solution of acetic acid containing just sufficient water to fully hydrolyze the amounts of acetyl halide recovered from the initial reaction and initial heating steps. Thus there is produced by such hydrolysis a glacial acetic acid suitable for reuse in the process as part of the initial reaction charge. If upon analysis the acetic acid product of this hydrolysis recovery step is found to contain more than the desired 1 to 3% water, then sufficient acetic anhydride can be added thereto to reduce the water content thereof to the desired amount.

A convenient method for determination of the water content of the glacial acetic acid produced by the above acetyl halide recovery procedure has been found to be measurement of the conductivity thereof. The conductivity, determined by a conventional conductivity probe, responds to the presence of water solution of HCl present in the reaction mixture and as the water concentration falls the conductivity decreases toward zero. A plot of the measured conductivity against analyzed water present affords a convenient means to determine the concentration of water, which is controlled to not more than 3% and preferably, to from 0.2% to 1% of water in the glacial acetic acid product.

The hydrogen halide (HCl or HBr) produced in the initial reaction and removed from the process in the first reaction step or in the subsequent initial heating step as well as that produced by the hydrolysis of the acetyl halide by-product in the recovery thereof can also be recovered, if desired, by absorbing the off gas from the hydrolysis and recovery of the acetyl halide in water, for example, by use of a water scrubber. The resulting aqueous solution of hydrogen halide is generally suitable for use in industrial applications of hydrochloric or hydrobromic acid aqueous solutions. Thus all by-products of the present process are effectively recoverable in a closed system and none need be released to the environment, a distinct advantage for the present novel process.

The present process can be carried out by various methods. For example, when operated as a batch-wise process the glacial acetic acid reactant can be charged to a suitable reaction vessel equipped with a stirrer and the phosphorus trihalide added either continuously or intermittently to the acetic acid under agitation and preferably below the surface thereof to avoid loss of the phosphorus trihalide reactant. Thereafter the reactants can be reacted, with moderate heating if required, to produce the liquid reaction product and evolve the acetyl halide and hydrogen halide by-products. The liquid reaction product is then further heated to elevated temperature with removal of residual by-products prior to reaction with the acetic anhydride to produce the normally solid anhydrous reaction product which is thereafter steam treated to recover the desired 1-hydroxy, ethylidene-1,1-diphosphonic acid. The batch process can be carried out in either one or two reaction vessels with associated finishing and storage vessels for adjustment of the solution concentration as desired. Likewise, the recovery of the by-product acetyl halide and steam stripped acetic acid is carried out in a hydrolysis vessel with associated packed column for countercurrent circulation of the aqueous acid solution in contact with the gaseous halides. The hydrogen halide by-product can be recovered by a water scrubbing column and associated receiving vessel.

The present process is well adapted to continuous operation whereby the reactants are continuously fed into suitable reaction vessels with the rate of feed of the reactants as well as other reaction conditions, such as temperature, used to insure the continuous withdrawal of the desired product. This can be accomplished by, for example, a series of four reaction vessels in which the liquid reaction product is prepared and the by-product acetyl halide and hydrogen halide is removed in the first vessel, then passed to a second vessel in which the product is heated under elevated temperature conditions and reacted with acetic anhydride to prepare the normally solid anhydrous reaction product which product is thereafter preferably passed to a series of two vessels in which the addition of water, if desired, and the steaming step can be performed for recovery of the desired product and removal of the acetic acid by-product. Substantially all of the acetic acid by-product is removed in the first of such steam stripping vessels in order that a relatively concentrated aqueous solution can be recovered for subsequent reaction with the by-product acetyl halide as discussed above. Additional dilution and storage vessels can be supplied as desired for the 1-hydroxy, ethylidene-1,1-diphosphonic acid product. Likewise the hydrolysis and recovery of the acetyl halide and absorption and recovery of the hydrogen halide can be carried out in the same equipment described above in connection with the batch process suitably sized for continuous operation.

The present process when combining the recovery of the by-product acetyl halide and by-product acetic acid streams with either batch or continuous operation of the process for producing the desired 1-hydroxy, ethylidene-1,1-diphosphonic acid possesses many advantages for industrial application. As noted above, the process is a fully closed loop providing for the release of substantially no reactants or by-products to the environment. Furthermore, the acid values of the by-product acetyl halide, the by-product acetic acid and the by-product hydrogen halide are recovered for sale or reuse which renders the process economically most attractive. Still further, the novel process provides an increased safety factor in that substantial quantities of hazardous toxic acid halides are not allowed to collect in the system. Moreover the novel process provides for a much increased throughput of reactants and yield of desired products with no increase in cycle time associated therewith.

The following examples are presented to illustrate the invention and parts by weight are used in the examples unless otherwise specified.

EXAMPLE I

A charge of about 250 parts of glacial acetic acid is placed in a suitable reaction vessel and heated to about 60°–70°C. About 1100 parts of $PCl_3$ and 1350 parts of acetic acid are fed at constant rates over a period of about 155 minutes while the temperature is maintained by heating at from 60°–68°C. Over the same period there is continuously fed at a constant rate a total of 1.0 ml. of a polysiloxane antifoam agent, SAG 470. The single-phase clear liquid reaction product rapidly evolves acetyl chloride and HCl at this temperature. Upon completion of the addition of the reactants the clear, single-phase liquid reaction product is heated to 115°C. over a period of about 80 minutes during which a very little additional acetyl chloride and HCl is evolved. The total acetyl chloride recovered by condensation during the initial reaction periods is found to be about 1140 parts and some 70 parts during the heat up period. The total HCl recovered by water scrubbing is found to be about 255 parts during the initial reaction and about 35 parts during heat up. When the liquid reaction product has reached about 115°C. additional below the liquid surface of about 360 parts of acetic anhydride is begun and completed over a period of about 65 minutes while controlling the temperature at between 115°C. and 125°C. The reaction product becomes very viscous indicating the formation of the normally solid anhydrous reaction product. For completion of the reaction the reaction product is then maintained at from 115°C to 125°C for 60 minutes. Samples submitted to $P^{31}$NMR analysis show about 1% of free phosphorous acid in the reaction product. The desired product, 1-hydroxy, ethylidene-1,1-diphosphonic acid is recovered by adding to the thick solution about 100 parts of water over a 60 minute period at a rate sufficient to control the exotherm and prevent boilover. The clear much less viscous liquid is then steam sparged at about 60 minutes which results in separation and condensation of the acetic acid present in the reaction product and a water solution of the desired 1-hydroxy, ethylidene-1,1-diphosphonic acid product.

A portion of the acetyl chloride condensate collected to a total of 566 parts of acetyl chloride is reacted with 416 parts of a 69% solution of aqueous acetic acid recovered from the hydrolysis and steam sparging of the reaction product to form glacial acetic acid suitable for reuse in the initial reaction. The acetyl chloride recovery reaction is conducted without external heating or cooling by adding the acetyl chloride gradually to the surface of the stirred aqueous acetic acid. The temperature initially rises from 24°C. to 69°C. during the addition of the first 100 parts of acetyl chloride and thereafter gradually decreases to about 40°C. A total of 193 parts of HCl is evolved at a steady rate during the entire addition of the acetyl chloride reactant and is collected in a water scrubber. The water remaining in the reaction mixture is determined by measuring the conductivity thereof and upon completion of the addition indicates no residual water. Addition to the glacial acetic acid product of 17 parts of water results in a final acetic acid solution containing 0.2% by weight of water which is suitable for recharge to a subsequent preparation.

EXAMPLE II

A charge of about 250 parts of glacial acetic acid is placed in a suitable reaction vessel and heated to about 70° to 80°C. About 2160 parts of $PBr_3$ and 1350 parts of acetic acid are fed over a period of about 200 minutes while the temperature is maintained at from 70°–80°C. by heating. There is rapidly evolved from the single-phase liquid reaction product acetyl bromide and HBr. When addition of the reactants is completed, the reaction product is heated to about 115°C. over a 90-minute period, during which some small additional amounts of acetyl bromide and HBr are evolved and collected. When the temperature of the reaction product reaches 100°C. to 115°C., addition of about 320 parts of acetic anhydride is begun and completed in a period of about 85 minutes while maintaining the temperature at from about 115°C. to 125°C., producing a normally solid anhydrous reaction product. After a holding period of about 25 minutes at 120°C., the desired 1-hydroxy, ethylidene-1,1-diphosphonic acid is recovered from the very thick reaction mixture by the addition of about 100 parts of water at a rate to control the temperature at about 120°–140°C. followed by steam sparging while the reaction mixture is maintained at about 135°C. to 140°C. for a period of about 60 minutes.

EXAMPLE III

The following illustrates operation of the process in a continuous manner. A continuous charge of about 41.6 parts per minute of acetic acid, about 28.3 parts per minute of $PCl_3$ and 30 ppm of Antifoam SAG 470, based upon the weight of the final desired product, is maintained in a suitable reaction vessel over an average dwell period of about 100 minutes under agitation and heated to a temperature of from 60°C. to 70°C. There is continuously evolved a stream of acetyl chloride and HCl which is continuously contacted in a separate vessel with an aqueous acetic acid stream for absorption of the acetyl chloride and conversion thereof to acetic acid and HCl, which is evolved and absorbed in a separate water scrubber. The clear single-phase reaction product, after the initial dwell period, is continuously withdrawn from the reaction vessel and passed to another suitable reaction vessel where it is heated to a temperature of from 115°C. to 125°C. thereby evolving additional acetyl chloride and HCl, which is directed to the same absorbers, and continuously contacted with a charge of acetic anhydride at about 8.7 parts per minute over an average dwell period of about 40 minutes. The reaction product is then continuously passed to a third reaction vessel where it is continuously contacted with about 0.5 part of water and sparged with about 7 parts of steam per minute while maintained at a temperature of about 125°C. to 130°C. for an average dwell period of about 40 minutes. There is continuously distilled about 19 parts of acetic acid and about 7 parts of water per minute, which is condensed and collected to produce an aqueous condensate of about 70–75% acetic acid. The collected condensate serves as a source of the acetic acid employed to absorb acetyl chloride evolved from the first reaction vessel, which produces a stream of 41.3 parts of glacial acetic acid per minute which is collected, adjusted, if necessary, to a water content of 1% or less by addition of acetic anhydride and then recycled as feed to the initial reaction vessel. From the third reaction vessel the product is continuously passed to a fourth suitable reaction vessel where it is sparged with about 7 parts per minute of steam at a temperature of about 135°C. to 140°C. for a period of about 40 minutes to produce the desired 1-hydroxy, ethylidene-1,1-diphosphonic acid product.

While this invention has been described with respect to various specific examples and embodiments, it is to be understood that the invention is not limited thereto and that it can be variously practiced within the scope of the following claims.

What is claimed is:

1. A process for preparing a 1-hydroxy, ethylidene-1,1-diphosphonic acid which comprises the steps of:
   1. reacting at a temperature of from about 50°C. to 80°C. in a reaction zone glacial acetic acid and a phosphorus trihalide selected from the group consisting of phosphorus tribromide and phosphorus trichloride in a molar ratio of at least about 2.5:1 in an homogenous, single-phase liquid reaction mixture, while continuously removing by-product acetyl halide as formed from said reaction zone,
   2. heating said reaction mixture to a temperature of from about 90°C. to 140°C.,
   3. adding and reacting with said reaction mixture at said temperature acetic anhydride in a molar ratio of from about 0.3 to 0.6 anhydride to phosphorus trihalide charged into the initial reaction, whereby a normally solid anhydrous reaction product is formed, and
   4. thereafter hydrolyzing said normally solid anhydrous reaction product by steaming to recover said 1-hydroxy, ethylidene-1,1-diphosphonic acid.

2. The process of claim 1 wherein the molar ratio of glacial acetic acid to phosphorus trihalide is from about 3.1 to 3.5:1.

3. The process of claim 1 wherein the molar ratio of acetic anhydride to phosphorus trihalide is from about 0.40 to 0.50.

4. The process of claim 1 wherein the phosphorus trihalide is phosphorus trichloride.

5. The process of claim 1 wherein the phosphorus trihalide is phosphorus tribromide.

6. The process of claim 1 wherein there is charged to the initial reaction zone a silicone antifoam agent in an amount of from about 10 to about 200 ppm, based on the weight of said diphosphonic acid product.

7. The process of claim 6 wherein said silicone antifoam agent is polydimethyl siloxane.

8. A process for preparing a 1-hydroxy, ethylidene-1,1-diphosphonic acid which comprises the steps of:
   1. reacting at a temperature of from about 50°C. to 80°C. in a reaction zone glacial acetic acid and a phosphorus trihalide selected from the group consisting of phosphorus tribromide and phosphorus trichloride in a molar ratio of at least about 2.5:1 in a homogenous, single-phase liquid reaction mixture, while continuously removing by-product acetyl halide as formed from said reaction zone,
   2. heating said reaction mixture to a temperature of from about 90°C. to 140°C.,
   3. adding and reacting with said reaction mixture at said temperature acetic anhydride in a molar ratio of from about 0.3 to about 0.6 anhydride to phosphorus trihalide charged into the initial reaction, whereby a normally solid anhydrous reaction product is formed,
   4. thereafter hydrolyzing said normally solid reaction product by steaming to recover said 1-hydroxy, ethylidene-1,1-diphosphonic acid and remove by-product acetic acid, and
   5. reacting said by-product acetyl halide from (1) with said aqueous by-product acetic acid by-product from (4) so as to produce an acetic acid containing less than 3% water.

9. The process of claim 8 wherein the acetic acid from (5) is recycled to and reacted in (1).

10. The process of claim 8 wherein the acetic acid from (5) contains less than 1% water.

11. The process of claim 8 wherein the molar ratio of glacial acetic acid to phosphorus trihalide is from about 3.1 to 3.5:1.

12. The process of claim 8 wherein the molar ratio of acetic anhydride to phosphorus trihalide is from about 0.40 to 0.50.

13. The process of claim 8 wherein the phosphorus trihalide is phosphorus trichloride.

14. The process of claim 8 wherein the phosphorus trihalide is phosphorus tribromide.

15. The process of claim 8 wherein there is charged to the initial reaction (1) a silicone antifoam agent in an amount of from about 10 to about 200 ppm, based on the weight of said diphosphonic acid product.

16. The process of claim 15 wherein said silicone antifoam agent is polydimethyl siloxane.

17. The process of claim 15 wherein said silicone antifoam agent is charged continuously to said reaction (1).

18. The process according to claim 1 wherein the process steps are carried out in a continuous manner.

19. The process according to claim 8 wherein the process steps are carried out in a continuous manner.

20. The process according to claim 18 wherein said trihalide is phosphorus trichloride.

21. The process according to claim 19 wherein said phosphorus trihalide is phosphorus trichloride.

* * * * *